United States Patent
Tomaru

(10) Patent No.: US 7,294,826 B2
(45) Date of Patent: Nov. 13, 2007

(54) BIO-SENSING APPARATUS

(75) Inventor: Yuichi Tomaru, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 60 days.

(21) Appl. No.: 11/368,519

(22) Filed: Mar. 7, 2006

(65) Prior Publication Data

US 2006/0204402 A1 Sep. 14, 2006

(30) Foreign Application Priority Data

Mar. 7, 2005 (JP) ............................. 2005-062589

(51) Int. Cl.
*G01N 21/00* (2006.01)

(52) U.S. Cl. .................. 250/236; 250/234; 250/461.2; 422/82.05

(58) Field of Classification Search ........ 250/234–236, 250/221, 222.1, 461.2; 422/82.05, 82.08, 422/82.09; 435/7.1; 356/445
See application file for complete search history.

(56) References Cited

U.S. PATENT DOCUMENTS 5,822,073 A * 10/1998 Yee et al. ................... 356/445
2002/0177161 A1 * 11/2002 Latov et al. ................. 435/7.1

FOREIGN PATENT DOCUMENTS

| JP | 9-257699 A | 10/1997 |
| JP | 2004-232027 A | 8/2004 |
| WO | WO 94/18544 A1 | 8/1994 |
| WO | WO 2004/113880 A2 | 12/2004 |

OTHER PUBLICATIONS

Takayuki Okamoto, et al., "Local Plasmon Sensor with Gold Colloid Monolayers Deposited Upon Glass Substrates", Optics Letters, vol. 25, No. 6, pp. 372-374, Mar. 15, 2000.

* cited by examiner

Primary Examiner—Kevin Pyo
(74) Attorney, Agent, or Firm—Sughrue Mion, PLLC

(57) ABSTRACT

A multi-channel sensor is provided with sensor sections, each of the sensor sections reflecting or transmitting light, whose physical characteristics vary for different kinds of samples. Each of samples is supported by one of the sensor sections. A scanning mirror scans the sensor sections of the multi-channel sensor with measuring light. A scanning controller controls the scanning mirror and stores information, which represents scanning positions of the measuring light with respect to the multi-channel sensor. A detector receives reflected light or transmitted light, which is radiated out from each of the sensor sections when each of the sensor sections is scanned with the measuring light. The detector thus detects the physical characteristics of the reflected light or the transmitted light.

8 Claims, 2 Drawing Sheets

BIO-SENSING APPARATUS

BACKGROUND OF THE INVENTION

1. Field of the Invention

This invention relates to a bio-sensing apparatus provided with a plurality of sensor sections, each of the sensor sections reflecting or transmitting light, whose physical characteristics vary for different kinds of samples. This invention particularly relates to a multi-channel bio-sensing apparatus capable of simultaneously performing measurements with respect to a plurality of samples with one time of sample setting.

2. Description of the Related Art

As bio-sensing apparatuses for use in analyses of biomolecules, there have heretofore been known bio-sensing apparatuses, wherein measuring light is irradiated to a sensor chip that reflects or transmits light, whose physical characteristics vary for different kinds of samples, and wherein physical characteristics of reflected light, which has been reflected from the sensor chip, or transmitted light, which has passed through the sensor chip, are detected. With the bio-sensing apparatuses, in cases where a measurement is performed in a state in which a known antigen (or a known antibody) has been bound to the sensor chip, a difference in physical characteristics of the reflected light or the transmitted light, which difference occurs in accordance with whether an antigen-antibody reaction has or has not occurred, is capable of being detected. In accordance with the results of the detection of the difference in physical characteristics of the reflected light or the transmitted light, it is possible to detect whether the antibody (or the antigen) is or is not contained in the sample. By way of example, certain kinds of the sensor chips utilize a phenomenon, in which the scattering or the absorption of light having a specific wavelength is enhanced by localized plasmon resonance, and the optical intensity of the light is thus attenuated.

For example, in order for the measurement efficiency to be enhanced, it is desired that the measurements with respect to a plurality of samples are capable of being performed with one time of sample setting. With the multi-channel sensing techniques described above, it is possible to perform analyses, wherein measurements with respect to the plurality of the samples are performed simultaneously, such that the basic conditions, such as the kind of a reference and the kind of the sample to be analyzed, are kept identical, and such that only a specific condition is altered, and wherein only the data obtained due to the difference in specific condition are analyzed.

A sensing apparatus has been proposed, wherein measuring light is irradiated collectively to a sensor chip, which is provided with a plurality of sensor sections (i.e., wells) located in an array form, and wherein physical characteristics of reflected light beams, which have been reflected from the sensor sections, are detected collectively by use of a detector provided with detecting devices located in an array form. The proposed sensing apparatus is disclosed in, for example, International Patent Publication No. WO/2004/113880.

With a multi-channel sensing operation, the measurements with respect to a plurality of samples may be performed simultaneously, such that the basic conditions are kept identical, and such that only the specific condition is altered. In such cases, in order for the data obtained due to the difference in specific condition are to be analyzed accurately, it is important that the measurement conditions do not vary markedly for different samples.

With the sensing apparatus disclosed in, for example, International Patent Publication No. WO/2004/113880, it is necessary for the measurements to be performed such that (a) the measuring light may be irradiated uniformly to all of the sensor sections on the sensor chip, such that (b) the position of each of the sensor sections and the position of the corresponding one of the detecting devices may be accurately matched with each other, and such that (c) the reflected light beam, which has been reflected from each of the sensor sections, may be detected so as to be free from adverse effects of (i.e., interference with) the reflected light beams, which have been reflected from the other sensor sections, through the setting of the pitches of the sensor sections at somewhat large pitches.

However, with the sensing apparatus disclosed in, for example, International Patent Publication No. WO/2004/113880, it is not always possible to satisfy all of the requirements described under (a), (b), and (c) appropriately, and therefore it is not always possible to perform accurate measurements. Also, as the number of the sensor sections becomes large, it will become more difficult to satisfy the requirements described under (a), (b), and (c). Therefore, limitation is imposed upon the number of sensing channels. Accordingly, under existing circumstances, a multi-channel bio-sensing technique for at least three channels has not yet been used in practice.

SUMMARY OF THE INVENTION

The primary object of the present invention is to provide a bio-sensing apparatus, which enables multi-channel sensing operations to be performed accurately, and which is capable of coping with measurements with multi-channels of at least three channels.

The present invention provides a bio-sensing apparatus, comprising:

i) measuring light radiating means for radiating out measuring light, ii) a multi-channel sensor provided with a plurality of sensor sections, each of the sensor sections reflecting or transmitting light, whose physical characteristics vary for different kinds of samples, each of a plurality of samples being supported by one of the plurality of the sensor sections, iii) a scanning mirror for scanning the plurality of the sensor sections of the multi-channel sensor with the measuring light, which has been radiated out from the measuring light radiating means, iv) scanning control means for controlling the scanning mirror and storing information, which represents scanning positions of the measuring light with respect to the multi-channel sensor, and v) detection means for receiving reflected light or transmitted light, which is radiated out from each of the plurality of the sensor sections when each of the plurality of the sensor sections is scanned with the measuring light, and detecting the physical characteristics of the reflected light or the transmitted light.

The term "multi-channel sensor" as used herein embraces both the sensor, which is constituted of one sensor chip provided with the plurality of the sensor sections, and the sensor, which is constituted of a plurality of sensor chips, each of the sensor chips being provided with at least one sensor section. Also, the plurality of the sensor sections of the multi-channel sensor need not necessarily be clearly partitioned from one another, and each of the samples may be applied to one of a plurality of regions of the multi-channel sensor at the time of the analyses. In such cases, the plurality of the regions of the multi-channel sensor correspond to the plurality of the sensor sections.

The bio-sensing apparatus in accordance with the present invention should preferably be modified such that the apparatus further comprises relative movement means for moving the multi-channel sensor with respect to the scanning mirror and in a direction different from the scanning direction of the scanning mirror, and storing information, which represents the relative movement position of the multi-channel sensor.

Also, the bio-sensing apparatus in accordance with the present invention should preferably be modified such that the multi-channel sensor comprises a flat sensor support section, the plurality of the sensor sections of the multi-channel sensor are arrayed in two-dimensional directions on the flat sensor support section, the scanning mirror uniaxially scans the plurality of the sensor sections of the multi-channel sensor with the measuring light, which has been radiated out from the measuring light radiating means, and the relative movement means uniaxially moves the flat sensor support section of the multi-channel sensor with respect to the scanning mirror and in the direction different from the scanning direction of the measuring light with the scanning mirror.

Further, the bio-sensing apparatus in accordance with the present invention should preferably be modified such that the multi-channel sensor comprises a flat sensor support section, the plurality of the sensor sections of the multi-channel sensor are arrayed in two-dimensional directions on the flat sensor support section, and the scanning mirror biaxially scans the plurality of the sensor sections of the multi-channel sensor with the measuring light, which has been radiated out from the measuring light radiating means.

Furthermore, the bio-sensing apparatus in accordance with the present invention should preferably be modified such that the multi-channel sensor comprises a circular cylinder-shaped sensor support section, the plurality of the sensor sections of the multi-channel sensor are arrayed on an inside circumferential surface of the circular cylinder-shaped sensor support section, the scanning mirror is constituted of a rotating mirror, which is located on a center axis of the circular cylinder-shaped sensor support section for rotation around the center axis of the circular cylinder-shaped sensor support section, and the relative movement means moves the circular cylinder-shaped sensor support section of the multi-channel sensor with respect to the scanning mirror and in the direction along the center axis of the circular cylinder-shaped sensor support section.

Also, the bio-sensing apparatus in accordance with the present invention should preferably be modified such that the detection means detects the reflected light, which is radiated out from each of the plurality of the sensor sections when each of the plurality of the sensor sections is scanned with the measuring light, and the apparatus further comprises a semi-transparent mirror, which is located between the scanning mirror and the multi-channel sensor, the semi-transparent mirror transmitting the measuring light and reflecting the reflected light, which has been radiated out from each of the plurality of the sensor sections, toward a direction different from the direction heading toward the scanning mirror.

Further, the bio-sensing apparatus in accordance with the present invention should preferably be modified such that each of the plurality of the sensor sections utilizes a phenomenon, in which an optical intensity of the reflected light having a specific wavelength becomes low due to localized plasmon resonance.

Furthermore, the bio-sensing apparatus in accordance with the present invention should preferably be modified such that the measuring light radiating means radiates out light, which has the specific wavelength, as the measuring light, and the detection means detects the optical intensity of the reflected light having the specific wavelength.

As will be understood from the specification, it should be noted that the term "moving a multi-channel sensor with respect to a scanning mirror" as used herein means movement of the multi-channel sensor relative to the scanning mirror, and embraces the cases wherein the multi-channel sensor is moved while the scanning mirror is kept stationary, the cases wherein the scanning mirror is moved while the multi-channel sensor is kept stationary, and the cases wherein both the multi-channel sensor and the scanning mirror are moved with respect to each other.

The bio-sensing apparatus in accordance with the present invention is provided with the scanning mirror for scanning the plurality of the sensor sections of the multi-channel sensor with the measuring light, which has been radiated out from the measuring light radiating means. Therefore, with the bio-sensing apparatus in accordance with the present invention, instead of the measuring light being irradiated collectively to the plurality of the sensor sections of the multi-channel sensor, the measuring light is irradiated successively to each of the plurality of the sensor sections of the multi-channel sensor during the scanning with the measuring light. Also, the reflected light or the transmitted light, which is radiated out from each of the plurality of the sensor sections when each of the plurality of the sensor sections is scanned with the measuring light, is received by the detection means. The physical characteristics of the reflected light or the transmitted light are thus capable of being detected.

Also, with the bio-sensing apparatus in accordance with the present invention, the same measuring light is irradiated to each of the plurality of the sensor sections of the multi-channel sensor. Therefore, the irradiating conditions, such as the optical intensity of the measuring light which impinges upon each of the plurality of the sensor sections of the multi-channel sensor, are kept identical with respect to the plurality of the sensor sections of the multi-channel sensor during the scanning with the measuring light. Further, instead of the reflected light or the transmitted light being radiated out from the plurality of the sensor sections simultaneously, the reflected light or the transmitted light is radiated out successively from the plurality of the sensor sections. Therefore, the reflected light or the transmitted light, which is radiated out from each of the plurality of the sensor sections, is capable of being detected as independent light without being adversely affected by the reflected light or the transmitted light, which is radiated out from the other sensor sections. Also, it is sufficient for the detection means to be of a simple constitution. Further, the position of each of the plurality of the sensor sections and the position of the detection means need not be strictly matched with each other.

Further, with the bio-sensing apparatus in accordance with the present invention, the measuring light is capable of being irradiated under identical conditions to each of the plurality of the sensor sections, and the reflected light or the transmitted light, which is radiated out from each of the plurality of the sensor sections, is capable of being detected as independent light without being adversely affected by the reflected light or the transmitted light, which is radiated out from the other sensor sections. Therefore, the multi-channel sensing operations are capable of being performed accurately.

Furthermore, with the bio-sensing apparatus in accordance with the present invention, the effects described above are capable of being obtained regardless of the number of the sensor sections and the pitches of the sensor sections. Therefore, no limitation is imposed upon the number of the sensor sections. Accordingly, the measurements with multi-channels of at least three channels are capable of being performed accurately. Also, the bio-sensing apparatus in accordance with the present invention is capable of coping with the measurements with a number of sensing channels, which number is markedly larger than the number of sensing channels possible with the sensing apparatus disclosed in, for example, International Patent Publication No. WO/2004/113880.

DESCRIPTION OF THE PREFERRED EMBODIMENTS

The present invention will hereinbelow be described in further detail with reference to the accompanying drawings.

First Embodiment

Figure 1A:
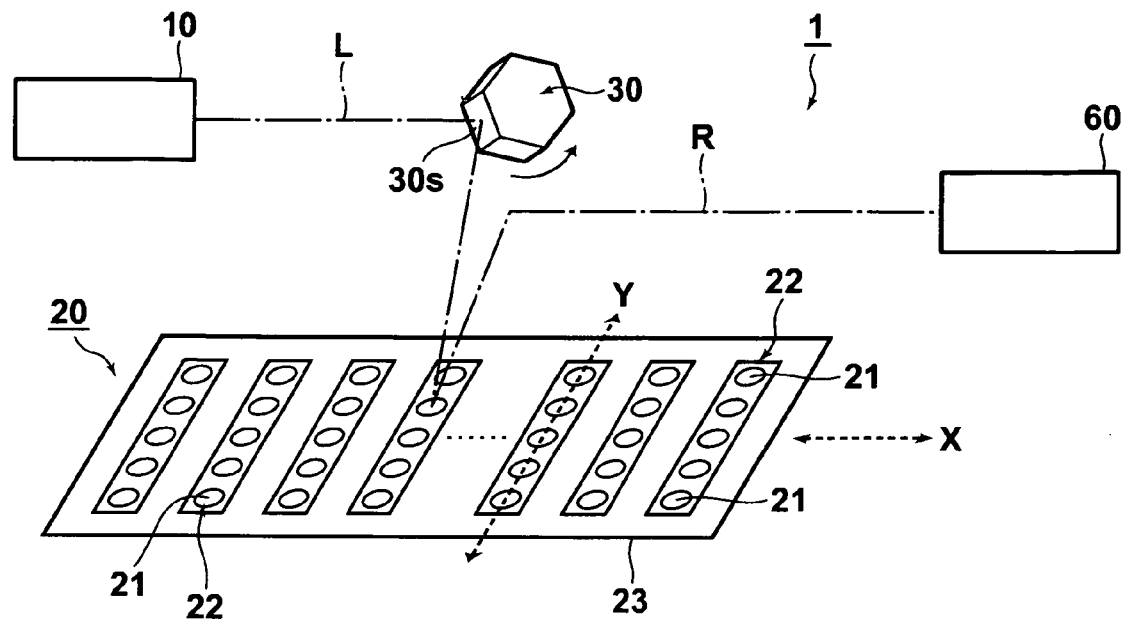
FIG. 1A is a perspective view showing major constituent elements of a first embodiment of, the bio-sensing apparatus in accordance with the present invention.
Figure 1B:
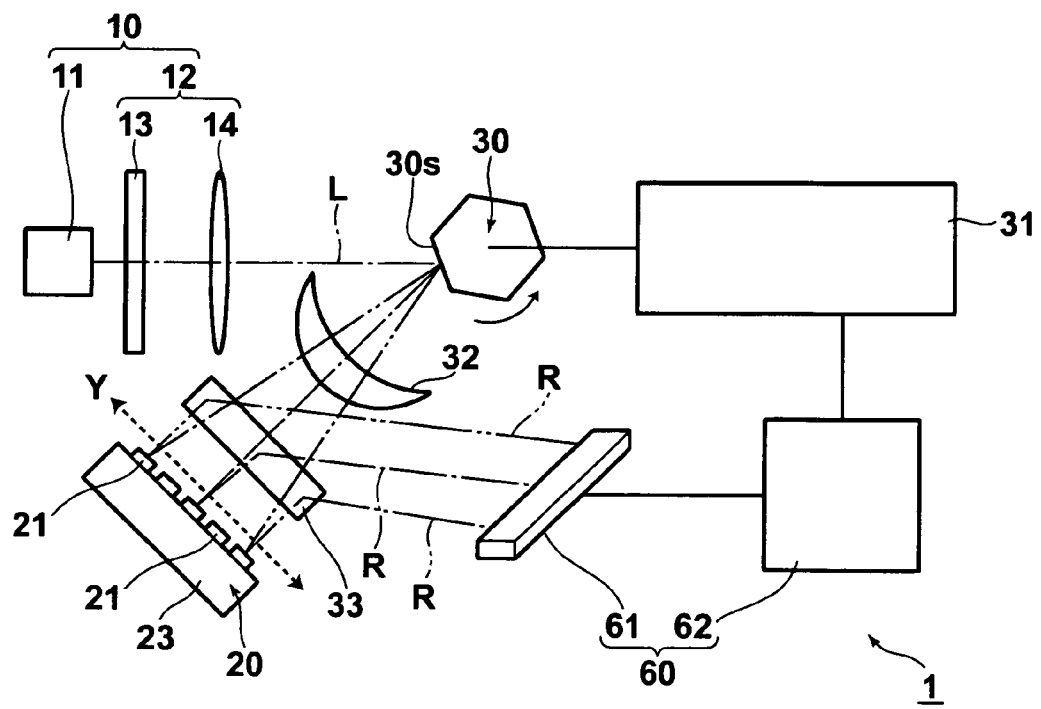
FIG. 1B is a schematic view showing the first embodiment of the bio-sensing apparatus in accordance with the present invention.

A first embodiment of the bio-sensing apparatus in accordance with the present invention will be described hereinbelow with reference to FIG. 1A and FIG. 1B. The first embodiment of the bio-sensing apparatus in accordance with the present invention is constituted as a multi-channel bio-sensing apparatus with at least three channels. FIG. 1A is a perspective view showing major constituent elements of a first embodiment of the bio-sensing apparatus in accordance with the present invention. FIG. 1B is a schematic view showing the first embodiment of the bio-sensing apparatus in accordance with the present invention. In FIG. 1B, sensor chips 22, 22, . . . are omitted for clearness, and sensor sections 21, 21, . . . are illustrated. The single-dot chained line in FIG. 1A and FIG. 1B and the double-dot chained lines in FIG. 1B represent the optical paths.

With reference to FIG. 1A and FIG. 1B, a bio-sensing apparatus 1, which is the first embodiment of the bio-sensing apparatus in accordance with the present invention, comprises measuring light radiating means 10 for radiating out measuring light L. The bio-sensing apparatus 1 also comprises a multi-channel sensor 20 provided with a plurality of the sensor sections 21, 21, . . . . Each of the sensor sections 21, 21, . . . Reflects light, whose physical characteristics vary for different kinds of samples. Each of a plurality of samples is supported by one of the plurality of the sensor sections 21, 21, . . . . The bio-sensing apparatus 1 further comprises a rotating polygon mirror (i.e., a scanning mirror) 30 for scanning the plurality of the sensor sections 21, 21, . . . of the multi-channel sensor 20 with the measuring light L, which has been radiated out from the measuring light radiating means 10. The bio-sensing apparatus 1 still further comprises detection means 60 for receiving reflected light R, which is radiated out from each of the plurality of the sensor sections 21, 21, . . . of the multi-channel sensor 20 when each of the plurality of the sensor sections 21, 21, . . . is scanned with the measuring light L, and detecting the physical characteristics of the reflected light R.

As illustrated in FIG. 1B, the measuring light radiating means 10 is constituted of a light source 11 and alight guiding system 12. The light guiding system 12 adjusts the light, which has been radiated out from the light source 11, such that the light becomes appropriate for the measurements. Also, the light guiding system 12 guides the adjusted light toward the rotating polygon mirror 30. The light source 11 may be constituted of one of various kinds of light sources, such as a laser, which radiates out a laser beam having a single wavelength, and a white light source (e.g. a tungsten lamp), which radiates out broad light. By way of example, in cases where the laser is employed as the light source 11, the light guiding system 12 may be constituted of a collimator lens (not shown) for collimating the light having been radiated out from the light source 11, a polarizer 13 for converting the light, which has been radiated out from the light source 11, into a specific polarized light, and a converging lens 14 for converging the polarized light, which has been radiated out from the polarizer 13.

As illustrated in FIG. 1A, the multi-channel sensor 20 is provided with a flat sensor support section 23. A plurality of the sensor chips 22, 22, . . . , each of which takes on the form of a long strip, are supported on the flat sensor support section 23. Each of the sensor chips 22, 22, . . . is provided with the plurality of the sensor sections 21, 21, . . . . In this embodiment, the plurality of the sensor sections 21, 21, . . . are arrayed on each of the sensor chips 22, 22, . . . uniaxially along a major axis direction of each of the sensor chips 22, 22, . . . , which major axis direction is indicated by the arrow Y. Also, the plurality of the sensor chips 22, 22, . . . are arrayed uniaxially on the flat sensor support section 23 so as to stand side by side with respect to a minor axis direction of each of the sensor chips 22, 22, . . . , which minor axis direction is indicated by the arrow X. In this manner, the plurality of the sensor sections 21, 21, . . . are arrayed in two-dimensional directions on the flat sensor support section 23.

The rotating polygon mirror 30 is a rotating mirror having a polygonal shape. The rotating polygon mirror 30 is controlled by a rotating polygon mirror control device (i.e., the scanning control means) 31. The rotating polygon mirror 30 has a light reflecting surface 30s. The angle of the light reflecting surface 30s of the rotating polygon mirror 30 varies in accordance with the rotation of the rotating polygon mirror 30, and the direction to which the measuring light L is reflected from the light reflecting surface 30s is thereby varied. In this manner, uniaxial scanning with the measuring light L is performed. In this embodiment, by the rotation of the rotating polygon mirror 30, each of the sensor chips 22, 22, . . . is scanned with the measuring light L uniaxially along the major axis direction of each of the sensor chips 22, 22, . . . , which major axis direction is indicated by the arrow Y. In FIG. 1B, the double-dot chained lines represent examples of the optical paths, which are formed when the angle of the light reflecting surface 30s of the rotating polygon mirror 30 varies. Information, which represents the scanning position of the measuring light L with respect to the multi-channel sensor 20 during the scanning performed by the rotating polygon mirror 30, is stored in the rotating polygon mirror control device 31.

A lens 32 for converging the measuring light L having been reflected from the rotating polygon mirror 30, should preferably be located between the rotating polygon mirror 30 and the multi-channel sensor 20. The lens may be constituted of an $f_1\theta$ lens, or the like.

The flat sensor support section 23 is moved by sensor support section moving means (not shown), which acts as the relative movement means. The sensor support section moving means is constituted of a movable stage, on which the flat sensor support section 23 is located, and a control device for controlling the movement of the movable stage. The flat sensor support section 23 is thus capable of being moved in the minor axis direction of each of the sensor chips 22, 22, . . . , which minor axis direction is indicated by the arrow X. (The minor axis direction described above is different from the major axis direction of each of the sensor chips 22, 22, . . . , which major axis direction is indicated by the arrow Y and is the direction of the scanning with the measuring light L performed by the rotating polygon mirror 30.) With the constitution described above, the entire area of the multi-channel sensor 20 is capable of being moved with respect to the rotating polygon mirror 30 and in the minor axis direction of each of the sensor chips 22, 22, . . . , which minor axis direction is indicated by the-arrow X. The information, which represents the relative movement position of the multi-channel sensor 20, is stored in the sensor support section moving means.

In this embodiment, the rotating polygon mirror 30 uniaxially scans the plurality of the sensor sections 21, 21, . . . of the multi-channel sensor 20 with the measuring light L in the major axis direction of each of the sensor chips 22, 22, . . . , which major axis direction is indicated by the arrow Y. Also, the flat sensor support section 23 is uniaxially moved in the minor axis direction of each of the sensor chips 22, 22, . . . , which minor axis direction is indicated by the arrow X. As a result, the sensor sections 21, 21, . . . having been arrayed in the two-dimensional directions are biaxially scanned with the measuring light L.

Also, in this embodiment, a semi-transparent mirror 33 is located between the rotating polygon mirror 30 and the multi-channel sensor 20. The semi-transparent mirror 33 transmits the measuring light L and reflects the reflected light R, which has been radiated out from each of the plurality of the sensor sections 21, 21, . . . , toward a direction different from the direction heading toward the rotating polygon mirror 30. The reflected light R, which has been reflected from the semi-transparent mirror 33, is received by the detection means 60.

The detection means 60 comprises a detector 61 for receiving the reflected light R, which has been reflected from the semi-transparent mirror 33, and detecting the physical characteristics of the reflected light R. The detection means 60 also comprises a data processing device 62. No limitation is imposed upon the kinds of the physical characteristics of the reflected light R, which are to be detected by the detection means 60. Examples the physical characteristics of the reflected light R, which are to be detected by the detection means 60, include the optical intensity of light having a specific wavelength, an absorbance, and a distribution of wavelengths of light. The detector 61 is selected from various kinds of detectors in accordance with the physical characteristics to be detected, and the like. In cases where the physical characteristics to be detected are the optical intensity of light having a specific wavelength, a photodiode, a photodiode array, or the like, is employed as the detector 61.

The data processing device 62 receives the detection data obtained from the detector 61, the information, which represents the scanning position of the measuring light L and has been stored in the rotating polygon mirror control device 31, and the information, which represents the relative movement position of the multi-channel sensor 20 and has been stored in the sensor support section moving means (not shown). In accordance with the received information, the data processing device 62 performs processing for discriminating which detection data obtained from the detector 61 corresponds to which sensor section 21 among the plurality of the sensor sections 21, 21, . . . , and outputting the detection data with respect to each of the sensor sections 21, 21, . . . .

Examples of the bio-sensing operations performed with this embodiment will be described hereinbelow.

Each of the sensor sections 21, 21, . . . of the multi-channel sensor 20 may be selected from various kinds of sensor sections, which are capable of reflecting the light, whose physical characteristics vary for different kinds of samples. By way of example, each of the sensor sections 21, 21, . . . of the multi-channel sensor 20 may be a sensor section utilizing a phenomenon, in which the optical intensity of the reflected light having a specific wavelength becomes low due to localized plasmon resonance.

Examples of the sensor sections 21, 21, . . . utilizing the localized plasmon resonance include (A) a sensor section having a surface, on which a thin metal film (constituted of gold, silver, or the like) capable of causing the localized plasmon resonance to occur has been formed, and (B) a sensor section having a surface, which has a fine surface recess-protrusion structure, at least the surface recess-protrusion structure being constituted of a metal capable of causing the localized plasmon resonance to occur. (The sensor section having the surface, on which the thin metal film capable of causing the localized plasmon resonance to occur has been formed, as described under (A) is disclosed in, for example, Japanese Unexamined Patent Publication No. 9(1997)-257699.) Particularly, with the sensor section of the type described under (B), which has the surface recess-protrusion structure, free electrons at each of the protruding areas undergo resonance with an electric field of light and vibrate, a strong electric field occurs in the vicinity of the protruding area, and the localized plasmon resonance thus occurs efficiently.

Examples of the sensor sections of the type described under (B) include (B1) a sensor section comprising a metal body having a surface, on which a plurality of fine metal particles have been fixed, and (B2) a sensor section comprising a metal body having a surface, which is provided with recess areas and protruding areas, fine metal particles having been fixed to the recess areas. (The sensor section comprising the metal body having the surface, on which the plurality of the fine metal particles have been fixed, as described under (B1) is described in, for example, "Local Plasmon Sensor With Gold Colloid Monolayers Deposited Upon Glass Substrates" by Takayuki Okamoto et al., OPTICS LETTERS, Vol. 25, No. 6, pp. 372-374, Mar. 15, 2000. The sensor section comprising the metal body having the surface, which is provided with the recess areas and the protruding areas, the fine metal particles having been fixed to the recess areas, as described under (B2) is described in, for example, Japanese Unexamined Patent Publication No. 2004-232027.)

In cases where the measuring light L is irradiated to each of the sensor sections 21, 21, . . . utilizing the localized plasmon resonance as described above, the localized plasmon resonance occurs with respect to the light having a certain specific wavelength, and the scattering or the absorption of the light having the specific wavelength is enhanced markedly. As a result, with respect to the light having the specific wavelength, the optical intensity of the light reflected from the sensor section 21 becomes markedly low. The light wavelength (i.e., the resonance peak wavelength) associated with the occurrence of the localized plasmon resonance, and the extent of the scattering or the absorption of the light having the specific wavelength depend upon the refractive index of the sample located on the surface of the sensor section 21, and the like. For example, in cases where the refractive index of the sample located on the surface of the sensor section 21 is large, the resonance peak wavelength shifts to the long wavelength side, and the extent of the scattering or the absorption of the light having the specific wavelength becomes large. Therefore, the sample sensing operation is capable of being performed with the detection of (1) the resonance peak wavelength of the reflected light, (2) the shift of the resonance peak wavelength of the reflected light from the basic conditions, and (3) the optical intensity of the reflected light.

In cases where the measuring light radiating means 10 is the means for radiating out the broad light having wavelengths, which contain the resonance peak wavelength, a spectroscope, which separates the light into its spectral components and forms the wavelength distribution (the spectrum) of the light, or the like, may be employed as the detector 61. In such cases, it is possible to detect (1) the resonance peak wavelength of the reflected light, or (2) the shift of the resonance peak wavelength of the reflected light from the basic conditions.

In cases where the measuring light radiating means 10 is the means for radiating out the light having the specific wavelength, the photodiode for detecting the optical intensity of the light, or the like, may be employed as the detector 61. In such cases, it is possible to detect (3) the alteration in optical intensity of the reflected light due to the scattering or the absorption of the measuring light.

With the multi-channel sensor 20 utilizing the localized plasmon resonance, it is possible to perform, for example, the measurement of the refractive index of the sample, and the like, and the identification of the sample in accordance with the refractive index of a known sample. For example, in cases where the measurement is performed in the state in which a known antibody (or a known antigen) has been fixed to the sensor section 21, if a certain antigen (or a certain antibody) is contained in the sample, the binding of the known antibody (or the known antigen) and the certain antigen (or the certain antibody) with each other will occur, and the refractive index of the sample, or the like, will alter. Therefore, it is possible to perform the detection of the presence or absence of the certain antigen (or the certain antibody) in the sample, the identification of the certain antigen (or the certain antibody) contained in the sample, and the like. Also, one of a plurality of samples may be utilized as a reference sample, the data obtained with respect to the reference sample may be subtracted as a background from the data obtained with respect to a sample to be analyzed, and an alteration in physical characteristics of the reflected light R obtained with respect to the sample to be analyzed may thus be investigated with the passage of time. In this manner, a real time analysis of the antigen-antibody reaction, or the like, is capable of being performed easily.

As a different example of the sensor section 21, a sensor chip utilizing light interference may be employed. (The sensor chip utilizing the light interference is described in, for example, International Patent Publication No. WO/94/18544.)

As described above, this embodiment of the bio-sensing apparatus 1 in accordance with the present invention comprises the measuring light radiating means 10 for radiating out the measuring light L. The bio-sensing apparatus 1 also comprises the multi-channel sensor 20. The bio-sensing apparatus 1 further comprises the rotating polygon mirror (i.e., the scanning mirror) 30 for uniaxially scanning the plurality of the sensor sections 21, 21, . . . of the multi-channel sensor 20 with the measuring light L. The bio-sensing apparatus 1 still further comprises the sensor support section moving means (not shown) acting as the relative movement means for moving the multi-channel sensor 20 with respect to the rotating polygon mirror 30. The bio-sensing apparatus 1 also comprises the detection means 60 for receiving the reflected light R, which is radiated out from each of the plurality of the sensor sections 21, 21, . . . when each of the plurality of the sensor sections 21, 21, . . . is scanned with the measuring light L, and detecting the physical characteristics of the reflected light R.

With the bio-sensing apparatus 1 having the constitution described above, instead of the measuring light L being irradiated collectively to the plurality of the sensor sections 21, 21, . . . of the multi-channel sensor 20, the measuring light L is irradiated successively to each of the plurality of the sensor sections 21, 21, . . . of the multi-channel sensor 20 through the scanning with the measuring light L performed by the rotating polygon mirror 30 and the relative movement of the multi-channel sensor 20 with respect to the rotating polygon mirror 30. Also, the reflected light R, which is radiated out from each of the plurality of the sensor sections 21, 21, . . . when each of the plurality of the sensor sections 21, 21, . . . is scanned with the measuring light L, is received by the detection means 60. The physical characteristics of the reflected light R are thus capable of being detected.

Also, with this embodiment of the bio-sensing apparatus 1 in accordance with the present invention, the same measuring light L is irradiated to each of the plurality of the sensor sections 21, 21, . . . of the multi-channel sensor 20. Therefore, the irradiating conditions, such as the optical intensity of the measuring light L which impinges upon each of the plurality of the sensor sections 21, 21, . . . of the multi-channel sensor 20, are kept identical with respect to the plurality of the sensor sections 21, 21, . . . of the multi-channel sensor 20 during the scanning with the measuring light L. Further, instead of the reflected light R being radiated out from the plurality of the sensor sections 21, 21, . . . simultaneously, the reflected light R is radiated out successively from the plurality of the sensor sections 21, 21, . . . . Therefore, the reflected light R, which is radiated out from each of the plurality of the sensor sections 21, 21, ..., is capable of being detected as independent light without being adversely affected by the reflected light R, which is radiated out from the other sensor sections 21, 21, .... Also, it is sufficient for the detection means 60 to be of a simple constitution. Further, the position of each of the plurality of the sensor sections 21, 21, ... and the position of the detection means 60 need not be strictly matched with each other.

Further, with this embodiment of the bio-sensing apparatus 1 in accordance with the present invention, the measuring light L is capable of being irradiated under identical conditions to each of the plurality of the sensor sections 21, 21, ..., and the reflected light R, which is radiated out from each of the plurality of the sensor sections 21, 21, ..., is capable of being detected as independent light without being adversely affected by the reflected light R, which is radiated out from the other sensor sections 21, 21, .... Therefore, the multi-channel sensing operations are capable of being performed accurately.

Furthermore, with this embodiment of the bio-sensing apparatus 1 in accordance with the present invention, the effects described above are capable of being obtained regardless of the number of the sensor sections 21, 21, ... and the pitches of the sensor sections 21, 21, .... Therefore, no limitation is imposed upon the number of the sensor sections 21, 21, .... Accordingly, the measurements with multi-channels of at least three channels are capable of being performed accurately. Also, this embodiment of the bio-sensing apparatus 1 in accordance with the present invention is capable of coping with the measurements with a number of sensing channels, which number is markedly larger than the number of sensing channels possible with the sensing apparatus disclosed in, for example, International Patent Publication No. WO/2004/113880.

In the first embodiment of the bio-sensing apparatus 1 in accordance with the present invention, the flat sensor support section 23 is moved in parallel with the minor axis direction of each of the sensor chips 22, 22, ..., which minor axis direction is indicated by the arrow X. The multi-channel sensor 20 is thus moved with respect to the rotating polygon mirror 30. Alternatively, the flat sensor support section 23 and/or the rotating polygon mirror 30 maybe moved in parallel with the minor axis direction of each of the sensor chips 22, 22, ..., which minor axis direction is indicated by the arrow X. In such cases, the same effects as those described above are capable of being obtained.

Also, in the first embodiment of the bio-sensing apparatus 1 in accordance with the present invention, the rotating polygon mirror 30 for performing the uniaxial scanning with the measuring light L is employed as the scanning mirror. Alternatively, biaxial scanning with the measuring light L may be performed by the scanning mirror. For example, a plurality of planar galvanometer mirrors (not shown), which are controlled such that the angles of the light reflecting surfaces alter, maybe employed as the scanning mirror. Also, the measuring light L may be reflected successively from the plurality of the galvanometer mirrors, and the biaxial scanning with the measuring light L may thereby be performed. In cases where the biaxial scanning with the measuring light L is performed, the relative movement means for moving the multi-channel sensor 20 with respect to the scanning mirror need not necessarily be utilized. However, in cases where the biaxial scanning with the measuring light L is performed, the relative movement means for moving the multi-channel sensor 20 with respect to the scanning mirror should preferably be utilized. In such cases, the bio-sensing apparatus in accordance with the present invention is capable of coping with the measurements with a markedly large number of sensing channels.

Second Embodiment

Figure 2A:
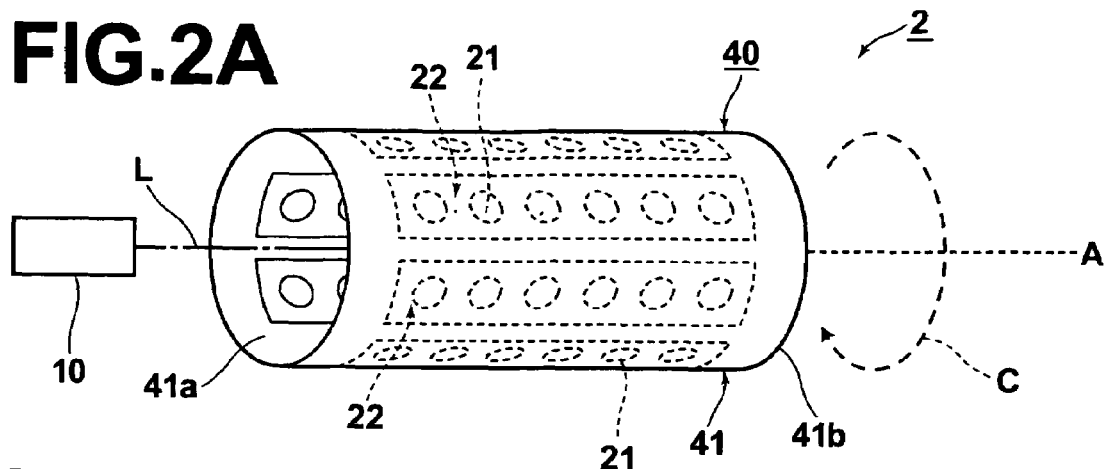
FIG. 2A is a perspective view showing major constituent elements of a second embodiment of the bio-sensing apparatus in accordance with the present invention.
Figure 2B:
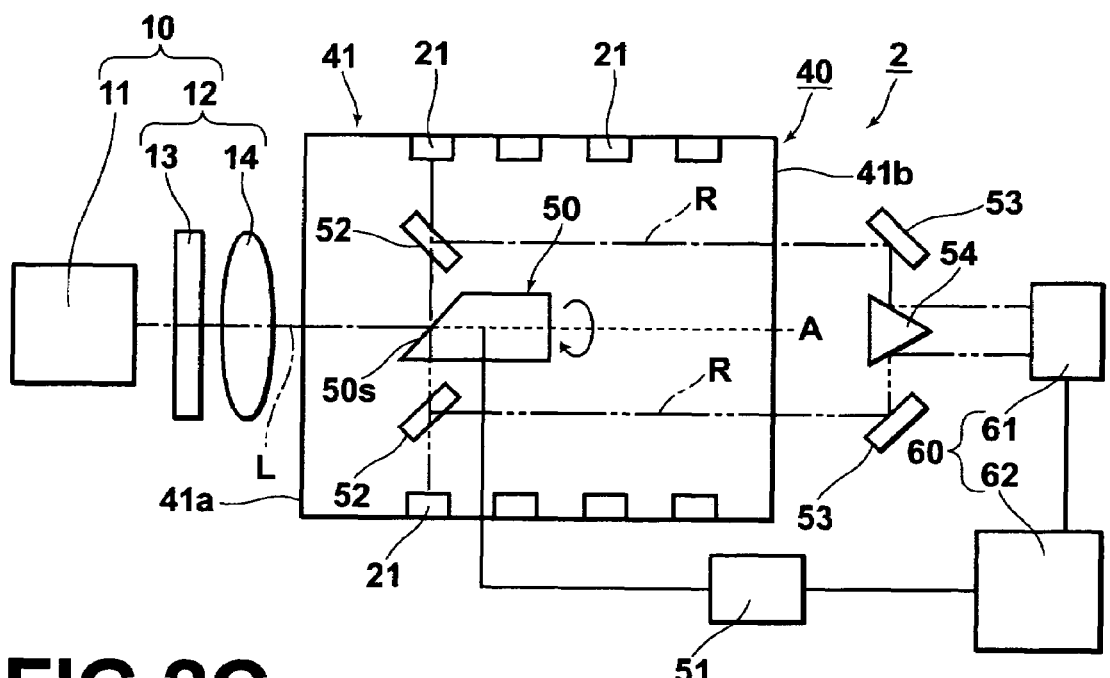
FIG. 2B is a schematic view showing the second embodiment of the bio-sensing apparatus in accordance with the present invention.
Figure 2C:
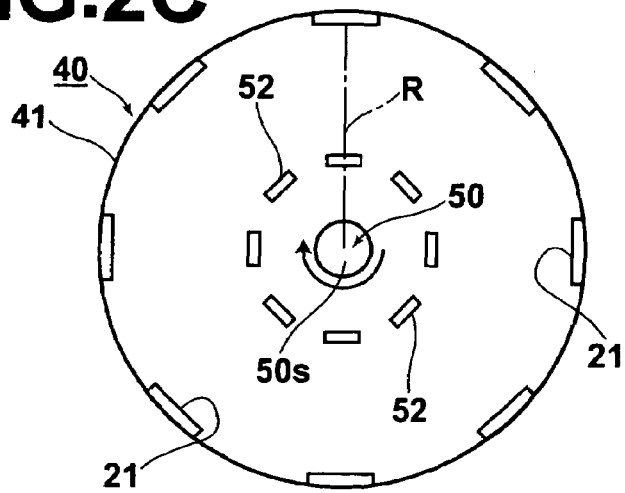
FIG. 2C is a side view showing a multi-channel sensor in the second embodiment of the bio-sensing apparatus in accordance with the present invention and an inside structure of the multi-channel sensor, the view being taken from a measuring light incidence side.

A second embodiment of the bio-sensing apparatus in accordance with the present invention will be described hereinbelow with reference to FIG. 2A, FIG. 2B, and FIG. 2C. As in the cases of the first embodiment described above, the second embodiment of the bio-sensing apparatus in accordance with the present invention is constituted as a multi-channel bio-sensing apparatus with at least three channels. FIG. 2A is a perspective view showing major constituent elements of a second embodiment of the bio-sensing apparatus in accordance with the present invention. FIG. 2B is a schematic view showing the second embodiment of the bio-sensing apparatus in accordance with the present invention. FIG. 2C is a side view showing a multi-channel sensor 40 in the second embodiment of the bio-sensing apparatus in accordance with the present invention and an inside structure of the multi-channel sensor 40, the view being taken from a measuring light incidence side. In FIG. 2B, the multi-channel sensor 40 is illustrated with a sectional view taken in a center axis direction. In FIG. 2B and FIG. 2C, the sensor chips 22, 22, ... are omitted for clearness, and the sensor sections 21, 21, ... are illustrated. Also, in FIG. 2A, FIG. 2B, and FIG. 2C, the number and the pitches of the sensor sections 21, 21, ... and the number and the pitches of the sensor chips 22, 22, ... are illustrated to be different for clearness. Further, in FIG. 2A, FIG. 2B, and FIG. 2C, similar elements are numbered with the same reference numerals with respect to FIG. 1A and FIG. 1B.

With reference to FIG. 2A, FIG. 2B, and FIG. 2C, a bio-sensing apparatus 2, which is the second embodiment of the bio-sensing apparatus in accordance with the present invention, comprises the measuring light radiating means 10 for radiating out the measuring light L. The bio-sensing apparatus 2 also comprises the multi-channel sensor 40 provided with a plurality of the sensor sections 21, 21, .... Each of the sensor sections 21, 21, .... Reflects light, whose physical characteristics vary for different kinds of samples. Each of a plurality of samples is supported by one of the plurality of the sensor sections 21, 21, .... The bio-sensing apparatus 2 further comprises a spinner mirror (i.e., a scanning mirror) 50 for scanning the plurality of the sensor sections 21, 21, ... of the multi-channel sensor 40 with the measuring light L, which has been radiated out from the measuring light radiating means 10. The bio-sensing apparatus 2 still further comprises the detection means 60 for receiving the reflected light R, which is radiated out from each of the plurality of the sensor sections 21, 21, ... of the multi-channel sensor 40 when each of the plurality of the sensor sections 21, 21, ... is scanned with the measuring light L, and detecting the physical characteristics of the reflected light R. The second embodiment of the bio-sensing apparatus in accordance with the present invention is constituted basically in the same manner as that for the aforesaid first embodiment, except that the constitution of the multi-channel sensor 40 is different from the constitution of the multi-channel sensor 20 and except that the spinner mirror 50 is utilized as the scanning mirror for performing the scanning with the measuring light L.

The multi-channel sensor 40 comprises a circular cylinder-shaped sensor support section 41, whose opposite ends are open. The plurality of the sensor chips 22, 22, ..., each of which takes on the form of a long strip, are supported on an inside circumferential surface of the circular cylinder-shaped sensor support section 41. Each of the sensor chips 22, 22, . . . is provided with the plurality of the sensor sections 21, 21, . . . . The constitution of each of the sensor chips 22, 22, . . . is identical with the constitution of each of the sensor chips 22, 22, . . . in the aforesaid first embodiment. Each of the sensor chips 22, 22, . . . is located such that the direction of the major axis of each of the sensor chips 22, 22, . . . is parallel with the direction of a center axis A of the circular cylinder-shaped sensor support section 41. Also, the plurality of the sensor chips 22, 22, . . . are arrayed so as to stand side by side with respect to a circumferential direction of the circular cylinder-shaped sensor support section 41, which circumferential direction is indicated by the arrow C.

The measuring light radiating means 10 and the multi-channel sensor 40 are designed such that the measuring light L enters into the circular cylinder-shaped sensor support section 41 from its one open end 41a and travels along the center axis A of the circular cylinder-shaped sensor support section 41.

The spinner mirror 50 is located such that its center axis may coincide with the center axis A of the circular cylinder-shaped sensor support section 41. The spinner mirror 50 is constituted of a rotating mirror having an approximately circular cylinder shape and having a light reflecting surface 50s, which is oblique with respect to the center axis A of the circular cylinder-shaped sensor support section 41. The spinner mirror 50 is capable of being moved around the center axis A of the circular cylinder-shaped sensor support section 41. The spinner mirror 50 is controlled by a spinner mirror control device 51, which acts as the scanning control means. The angle of the light reflecting surface 50s of the spinner mirror 50 alters in accordance with the rotation of the spinner mirror 50, and the direction to which the measuring light L is reflected is thus altered. As a result, the uniaxial scanning with the measuring light L is performed in the circumferential direction of the circular cylinder-shaped sensor support section 41, which circumferential direction is indicated by the arrow C. (Specifically, the uniaxial scanning with the measuring light L is performed in the array direction of the sensor chips 22, 22, . . . ) In FIG. 2B, the double-dot chained line represents the optical path, which is formed when the spinner mirror 50 has been rotated by an angle of 180° from the state illustrated in FIG. 2B. Information, which represents the scanning position of the measuring light L with respect to the multi-channel sensor 40 during the scanning performed by the spinner mirror 50, is stored in the spinner mirror control device 51.

The spinner mirror 50 is capable of being moved by spinner mirror moving means (not shown), which acts as the relative movement means, in the direction of the center axis A of the circular cylinder-shaped sensor support section 41. With the constitution described above, the multi-channel sensor 40 is capable of being subjected to the relative movement with respect to the spinner mirror 50 and in the direction of the center axis A of the circular cylinder-shaped sensor support section 41. Information, which represents the relative movement position of the multi-channel sensor 40, is stored in the spinner mirror moving means.

In the second embodiment, the spinner mirror 50 performs the uniaxial scanning with the measuring light L in the circumferential direction of the circular cylinder-shaped sensor support section 41, which circumferential direction is indicated by the arrow C. Also, the spinner mirror 50 is moved uniaxially in the direction of the center axis A of the circular cylinder-shaped sensor support section 41. As a result, the plurality of the sensor sections 21, 21, . . . having been arrayed on the inside circumferential surface of the circular cylinder-shaped sensor support section 41 are biaxially scanned with the measuring light L.

Also, in the second embodiment, a plurality of semi-transparent mirrors 52, 52, . . . are located between the spinner mirror 50 and the multi-channel sensor 40. Each of the semi-transparent mirrors 52, 52, . . . transmits the measuring light L and reflects the reflected light R, which has been radiated out from each of the plurality of the sensor sections 21, 21, . . . , toward a direction different from the direction heading toward the spinner mirror 50. The number of the semi-transparent mirrors 52, 52, . . . is identical with the number of the sensor chips 22, 22, . . . . . Each of the semi-transparent mirrors 52, 52, . . . is located between the light reflecting surface 50s of the spinner mirror 50 and one of the sensor chips 22, 22, . . . . Each of the semi-transparent mirrors 52, 52, . . . is moved in parallel in accordance with the parallel movement of the spinner mirror 50. The relationship between the position of each of the semi-transparent mirrors 52, 52, . . . and the position of the light reflecting surface 50s of the spinner mirror 50 is kept identical. The reflected light R, which has been reflected from each of the semi-transparent mirrors 52, 52, . . . , is radiated out from the other open end 41b of the circular cylinder-shaped sensor support section 41, reflected from mirrors 53 and 54, and received by the detection means 60.

The number of the semi-transparent mirrors 52, 52, . . . and the manner in which the semi-transparent mirrors 52, 52, . . . are moved may be designed in various ways. In cases where the semi-transparent mirrors 52, 52, . . . are utilized in a number equal to the number of the sensor sections 21, 21, the semi-transparent mirrors 52, 52, . . . need not be movable. Also, in cases where the semi-transparent mirrors 52, 52, . . . are located for rotation in the circumferential direction of the circular cylinder-shaped sensor support section 41, which circumferential direction is indicated by the arrow C, the number of the semi-transparent mirrors 52, 52, . . . is capable of being set to be smaller than the number of the sensor chips 22, 22, . . . . . Further, the light guide system for guiding the reflected light R from each of the semi-transparent mirrors 52, 52, . . . toward the detection means 60 may be designed in various other ways.

As in the aforesaid first embodiment, the detection means 60 is constituted of the detector 61 and the data processing device 62. The data processing device 62 receives the detection data obtained from the detector 61, the information, which represents the scanning position of the measuring light L and has been stored in the spinner mirror control device 51, and the information, which represents the relative movement position of the multi-channel sensor 40 and has been stored in the spinner mirror moving means (not shown). In accordance with the received information, the data processing device 62 performs the processing for discriminating which detection data obtained from the detector 61 corresponds to which sensor section 21 among the plurality of the sensor sections 21, 21, and outputting the detection data with respect to each of the sensor sections 21, 21, . . . .

The combination of the sensor sections 21, 21, . . . with the detection means 60 and examples of the bio-sensing operations performed with the second embodiment may be set in the same manner as that described with respect to the aforesaid first embodiment.

As described above, the second embodiment of the bio-sensing apparatus 2 in accordance with the present invention comprises the measuring light radiating means 10 for radiating out the measuring light L. The bio-sensing apparatus 2 also comprises the multi-channel sensor 40. The bio-sensing apparatus 2 further comprises the spinner mirror (i.e., the scanning mirror) 50 for uniaxially scanning the plurality of the sensor sections 21, 21, . . . of the multi-channel sensor 40 with the measuring light L in the circumferential direction of the circular cylinder-shaped sensor support section 41, which circumferential direction is indicated by the arrow C. The bio-sensing apparatus 2 still further comprises the spinner mirror moving means (not shown) acting as the relative movement means for subjecting the multi-channel sensor 40 to the relative movement with respect to the spinner mirror 50 in the direction of the center axis A of the circular cylinder-shaped sensor support section 41. The bio-sensing apparatus 2 also comprises the detection means 60 for receiving the reflected light R, which is radiated out from each of the plurality of the sensor sections 21, 21, . . . when each of the plurality of the sensor sections 21, 21, . . . is scanned with the measuring light L, and detecting the physical characteristics of the reflected light R.

With the bio-sensing apparatus 2 having the constitution described above, as in the aforesaid first embodiment, instead of the measuring light L being irradiated collectively to the plurality of the sensor sections 21, 21, . . . of the multi-channel sensor 20, the measuring light L is irradiated successively to each of the plurality of the sensor sections 21, 21, . . . of the multi-channel sensor 40 through the scanning with the measuring light L. Also, the reflected light R, which is radiated out from each of the plurality of the sensor sections 21, 21, . . . when each of the plurality of the sensor sections 21, 21, . . . is scanned with the measuring light L, is received by the detection means 60. The physical characteristics of the reflected light R are thus capable of being detected. Therefore, with the second embodiment, as in the aforesaid first embodiment, the multi-channel sensing operations are capable of being performed accurately. Also, no limitation is imposed upon the number of the sensor sections 21, 21, . . . . Accordingly, the measurements with multi-channels of at least three channels are capable of being performed accurately. Also, the second embodiment of the bio-sensing apparatus 2 in accordance with the present invention is capable of coping with the measurements with a number of sensing channels, which number is markedly larger than the number of sensing channels possible with the sensing apparatus disclosed in, for example, International Patent Publication No. WO/2004/113880.

In the second embodiment of the bio-sensing apparatus 2 in accordance with the present invention, the spinner mirror 50 is moved in parallel with the direction of the center axis A of the circular cylinder-shaped sensor support section 41. The multi-channel sensor 40 is thus subjected to the relative movement with respect to the spinner mirror 50. Alternatively, the circular cylinder-shaped sensor support section 41 and/or the spinner mirror 50 maybe moved in parallel with the direction of the center axis A of the circular cylinder-shaped sensor support section 41. In such cases, the same effects as those described above are capable of being obtained.

EXAMPLES OF DESIGN MODIFICATIONS

The bio-sensing apparatus in accordance with the present invention is not limited to the first and second embodiments described above and may be embodied in various other ways.

For example, the array of the sensor sections 21, 21, of the multi-channel sensor 20 or the multi-channel sensor 40, the mechanism for the scanning with the measuring light L, and the like, may be modified in various other ways.

Also, in each of the first and second embodiments described above, the multi-channel sensor 20 or the multi-channel sensor 40 is subjected to the relative movement with respect to the scanning mirror (i.e., the rotating polygon mirror 30 or the spinner mirror 50). Alternatively, the multi-channel sensor 20 or the multi-channel sensor 40 may be kept stationary with respect to the scanning mirror. With the constitution, in which the multi-channel sensor 20 or the multi-channel sensor 40 is kept stationary with respect to the scanning mirror, in cases Where-the plurality of the sensor sections 21, 21, . . . are located within the range capable of being scanned by use of the scanning mirror, the accurate multi-channel bio-sensing operations are capable of being performed as in the first and second embodiments described above. However, in cases where the multi-channel sensor 20 or the multi-channel sensor 40 is capable of being subjected to the relative movement with respect to the scanning mirror, the bio-sensing apparatus is capable of coping with the measurements with a large number of sensing channels.

Further, in each of the first and second embodiments described above, each of the sensor sections 21, 21, . . . . Reflects the light, whose physical characteristics vary for different kinds of samples, and the detection means 60 receives the reflected light R, which is radiated out from each of the sensor sections 21, 21, . . . . Alternatively, each of the sensor sections may transmit the light, whose physical characteristics vary for different kinds of samples, and the detection means may receive the transmitted light, which is radiated out from each of the sensor sections, and may detect the physical characteristics of the transmitted light. In cases where the transmitted light is detected, the semi-transparent mirror located between the scanning mirror and the multi-channel sensor need not be utilized. Also, in such cases, the detection means may be located at the position for receiving the transmitted light, which is radiated out from each of the sensor sections. Alternatively, in such cases, a mirror, or the like, may be located at the position for receiving the transmitted light, which is radiated out from each of the sensor sections, and the transmitted light may be guided by the mirror, or the like, toward the detection means.

INDUSTRIAL APPLICABILITY

The bio-sensing apparatus in accordance with the present invention is applicable to multi-channel bio-sensing operations, in which the measurements with respect to a plurality of samples are performed simultaneously under identical measurement conditions, and particularly multi-channel bio-sensing operations, in which the measurements with respect to at least three samples are performed simultaneously under identical measurement conditions.

What is claimed is:

1. A bio-sensing apparatus, comprising:
  i) measuring light radiating means for radiating out measuring light,
  ii) a multi-channel sensor provided with a plurality of sensor sections, each of the sensor sections reflecting or transmitting light, whose physical characteristics vary for different kinds of samples, each of a plurality of samples being supported by one of the plurality of the sensor sections,
  iii) a scanning mirror for scanning the plurality of the sensor sections of the multi-channel sensor with the measuring light, which has been radiated out from the measuring light radiating means, iv) scanning control means for controlling the scanning mirror and storing information, which represents scanning positions of the measuring light with respect to the multi-channel sensor, and v) detection means for receiving reflected light or transmitted light, which is radiated out from each of the plurality of the sensor sections when each of the plurality of the sensor sections is scanned with the measuring light, and detecting the physical characteristics of the reflected light or the transmitted light.

2. An apparatus as defined in claim 1 wherein the apparatus further comprises relative movement means for moving the multi-channel sensor with respect to the scanning mirror and in a direction different from the scanning direction of the scanning mirror, and storing information, which represents the relative movement position of the multi-channel sensor.

3. An apparatus as defined in claim 2 wherein the multi-channel sensor comprises a flat sensor support section, the plurality of the sensor sections of the multi-channel sensor are arrayed in two-dimensional directions on the flat sensor support section, the scanning mirror uniaxially scans the plurality of the sensor sections of the multi-channel sensor with the measuring light, which has been radiated out from the measuring light radiating means, and the relative movement means uniaxially moves the flat sensor support section of the multi-channel sensor with respect to the scanning mirror and in the direction different from the scanning direction of the measuring light with the scanning mirror.

4. An apparatus as defined in claim 1 wherein the multi-channel sensor comprises a flat sensor support section, the plurality of the sensor sections of the multi-channel sensor are arrayed in two-dimensional directions on the flat sensor support section, and the scanning mirror biaxially scans the plurality of the sensor sections of the multi-channel sensor with the measuring light, which has been radiated out from the measuring light radiating means.

5. An apparatus as defined in claim 2 wherein the multi-channel sensor comprises a circular cylinder-shaped sensor support section, the plurality of the sensor sections of the multi-channel sensor are arrayed on an inside circumferential surface of the circular cylinder-shaped sensor support section, the scanning mirror is constituted of a rotating mirror, which is located on a center axis of the circular cylinder-shaped sensor support section for rotation around the center axis of the circular cylinder-shaped sensor support section, and the relative movement means moves the circular cylinder-shaped sensor support section of the multi-channel sensor with respect to the scanning mirror and in the direction along the center axis of the circular cylinder-shaped sensor support section.

6. An apparatus as defined in claim 1 wherein the detection means detects the reflected light, which is radiated out from each of the plurality of the sensor sections when each of the plurality of the sensor sections is scanned with the measuring light, and the apparatus further comprises a semi-transparent mirror, which is located between the scanning mirror and the multi-channel sensor, the semi-transparent mirror transmitting the measuring light and reflecting the reflected light, which has been radiated out from each of the plurality of the sensor sections, toward a direction different from the direction heading toward the scanning mirror.

7. An apparatus as defined in claim 1 wherein each of the plurality of the sensor sections utilizes a phenomenon, in which an optical intensity of the reflected light having a specific wavelength becomes low due to localized plasmon resonance.

8. An apparatus as defined in claim 7 wherein the measuring light radiating means radiates out light, which has the specific wavelength, as the measuring light, and the detection means detects the optical intensity of the reflected light having the specific wavelength.

* * * * *